(12) United States Patent
Yang

(10) Patent No.: US 11,772,021 B2
(45) Date of Patent: Oct. 3, 2023

(54) WALL-MOUNTED AIR PURIFIER

(71) Applicant: SHENZHEN ANTOP TECHNOLOGY CO., LTD, Shenzhen (CN)

(72) Inventor: Ruidian Yang, Shenzhen (CN)

(73) Assignee: SHENZHEN ANTOP TECHNOLOGY CO., LTD, Shenzhen (CN)

( * ) Notice: Subject to any disclaimer, the term of this patent is extended or adjusted under 35 U.S.C. 154(b) by 235 days.

(21) Appl. No.: 17/195,687

(22) Filed: Mar. 9, 2021

(65) Prior Publication Data

US 2022/0176292 A1   Jun. 9, 2022

(30) Foreign Application Priority Data

Dec. 9, 2020   (CN) .......................... 202022932372.1
Dec. 9, 2020   (CN) .......................... 202022939412.5

(51) Int. Cl.
*B01D 46/00*   (2022.01)
*B01D 46/10*   (2006.01)
*A61L 9/20*   (2006.01)

(52) U.S. Cl.
CPC ............ *B01D 46/0028* (2013.01); *A61L 9/20* (2013.01); *B01D 46/0006* (2013.01); *B01D 46/0049* (2013.01); *B01D 46/10* (2013.01); *A61L 2209/12* (2013.01); *A61L 2209/14* (2013.01); *B01D 2273/30* (2013.01); *B01D 2279/65* (2013.01)

(58) Field of Classification Search
CPC ............ B01D 46/0028; B01D 46/0006; B01D 46/004; B01D 46/09; B01D 46/10; B01D 2273/30; B01D 2273/65; B01D 46/0049; A61L 9/20; A61L 2209/12; A61L 2209/14
USPC .......................................................... 96/224
See application file for complete search history.

(56) References Cited

U.S. PATENT DOCUMENTS 5,225,167 A * 7/1993 Wetzel ...................... F24F 8/22
                                                  250/492.1
5,997,619 A * 12/1999 Knuth ................ B01D 46/0038
                                                  55/385.2

(Continued)

FOREIGN PATENT DOCUMENTS

CN    105276693 A  *  1/2016
CN    109992064 A  *  7/2019

(Continued)

*Primary Examiner* — Robert A Hopkins
*Assistant Examiner* — Qianping He
(74) *Attorney, Agent, or Firm* — CANTOR COLBURN LLP

(57) ABSTRACT

This application provides a wall-mounted air purifier, including a casing, a filter mounted in the casing, and a fan mounted in the casing. The casing is provided with an air inlet and an air outlet, and the air outlet is located at the position corresponding to the outlet of the fan, the filter is located between the air inlet and the fan, an ultraviolet light source is also mounted in the casing, and the ultraviolet light source is arranged between the air inlet and the fan. The wall-mounted air purifier provided in the present application filters and purifies the air by providing a filter in the casing; and an ultraviolet light source is mounted in the casing to sterilize and disinfect the gas entering the air inlet and purify the air, improve air purification capacity.

16 Claims, 11 Drawing Sheets

(56) References Cited

U.S. PATENT DOCUMENTS

| | | | | |
|---|---|---|---|---|
| 2007/0045561 A1* | 3/2007 | Cooper | ............... | C02F 1/325 |
| | | | | 250/453.11 |
| 2012/0199005 A1* | 8/2012 | Koji | ............... | F24F 8/22 |
| | | | | 96/224 |
| 2013/0052090 A1* | 2/2013 | Bohlen | ............... | B01D 53/885 |
| | | | | 422/121 |
| 2016/0184753 A1* | 6/2016 | Chu | ............... | B01D 46/58 |
| | | | | 55/467 |

FOREIGN PATENT DOCUMENTS

| | | | | |
|---|---|---|---|---|
| CN | 111396333 A | * | 7/2020 | |
| JP | 2004166996 A | * | 6/2004 | |

* cited by examiner

WALL-MOUNTED AIR PURIFIER

CROSS-REFERENCE TO RELATED APPLICATIONS

Pursuant to 35 U.S.C. § 119 and the Paris Convention Treaty, this application claims the priority of the Chinese patent application filed at the Chinese Patent Office on Dec. 9, 2020, with the application number 202022939412.5 and the invention title "wall-mounted air purifier", and Chinese patent application filed at the Chinese Patent Office on Dec. 9, 2020, with the application number 202022932372.1 and the invention title "wall-mounted air purifier". the entire content of which are incorporated into this application by reference.

FIELD

This application relates to the technical field of air purification, and more specifically, relates to a wall-mounted air purifier.

BACKGROUND

Technical Field

This application relates to the technical field of air purification, and more specifically, relates to a wall-mounted air purifier.

Description of the Related Art

The statements here only provide background information related to this application, and do not necessarily constitute prior art. As people are more conscious of the environment, more and more air purifiers are used. The current air purifiers are clarified into floor-standing and wall-mounted type. Floor-standing air purifiers generally have air intake at the bottom or backside, and air outlet at the top or on the front. Wall-mounted air purifiers generally have air intake at the top and air outlet on the front or at the bottom. Wall-mounted air purifiers are generally mounted on the wall and will not occupy any floor space of the room, and are more and more favored by the users. However, currently, most wall-mounted air purifiers have filters in the casing which is used to filter the air, which has a weak ability to purify the air.

SUMMARY

The purpose of the embodiments of the present application is to provide a wall-mounted air purifier to solve the problem of a weak ability to purify the air of the wall-mounted air purifier in the related art.

In order to achieve the above purpose, the technical solution adopted in the embodiments of the present application is to provide a wall-mounted air purifier including a casing, a filter mounted in the casing, and a fan mounted in the casing. The casing is provided with an air inlet and an air outlet, the air outlet is located at a position corresponding to the outlet of the fan, the filter is located between the air inlet and the fan, and an ultraviolet light source is also mounted on the casing, and the ultraviolet light source is arranged between the air inlet and the fan.

The beneficial effects of the wall-mounted air purifier provided by the embodiments of the present application are: compared with the prior art, the wall-mounted air purifier of the present application filters and purifies the air by arranging a filter in the casing; and an ultraviolet light source is mounted in the casing to sterilize the gas entering the air inlet, so as to purify the air and improve the air purification capacity.

BRIEF DESCRIPTION OF THE DRAWINGS

In order to more clearly describe the technical solutions in the embodiments of the present application, the following will briefly introduce the accompanying drawings used in the description of the embodiments or exemplary technologies. Obviously, the accompanying drawings in the following description are only some embodiments of the present application, and those skilled in the art can obtain other drawings based on these drawings without creative work.

Figure 1:
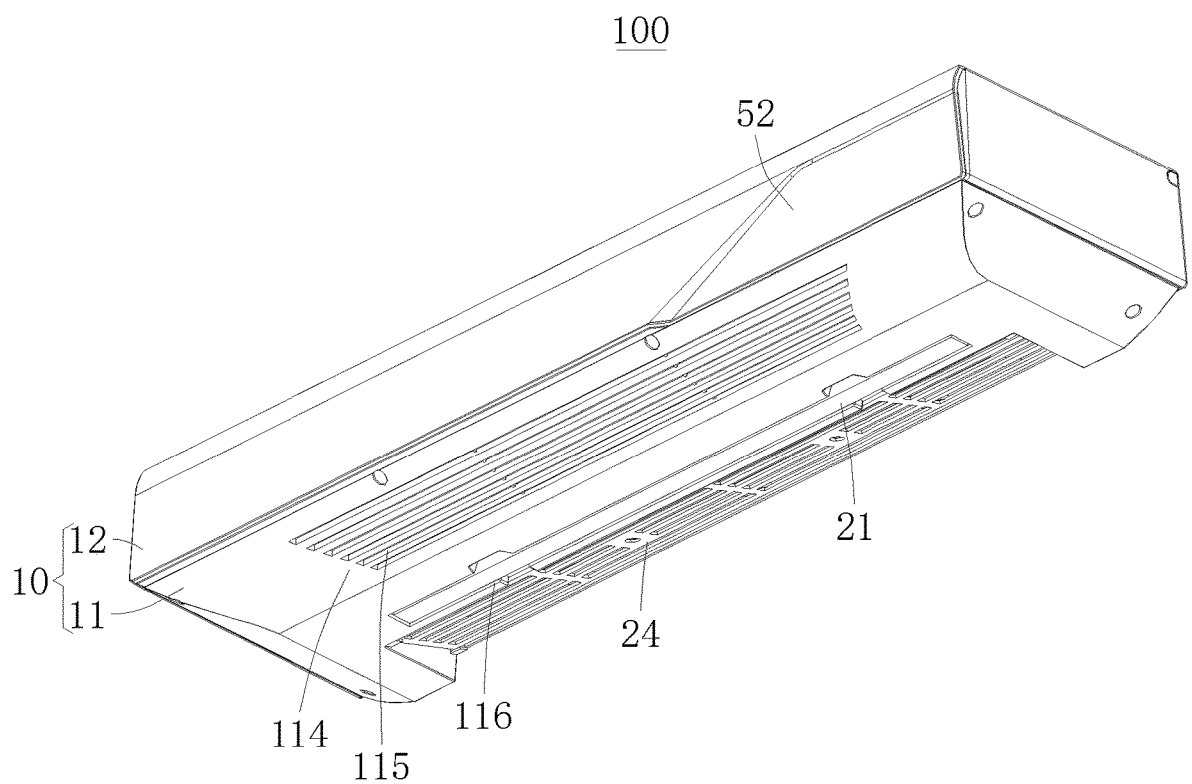
FIG. 1 is a schematic structural view of a wall-mounted air purifier provided in Embodiment 1 of the application.

In the drawings, the reference signs of the drawings are as follow:

100—wall—mounted air purifier;
10—casing; 11—bottom casing; 111—inclined surface; 112—air inlet; 113—baffle; 114—air outlet surface; 115—air outlet; 116—socket; 117—sliding plate; 12—housing shell; 121—wire concealing groove; 122—hanging snap; 123—window; 124—cover plate;

21—filter; 211—magnetic block; 212—magnetic member; 22—separator; 221—sliding grooves; 23—filter mesh; 24—grille plate;
31—fan; 311—wind hood; 312—tubular wind wheel; 313—motor;
41—ultraviolet light source; 411—ultraviolet lamp tube; 412—lamp holder; 413—ultraviolet LED module; 42—light shield; 421—vent; 422—first opening; 423—blocking piece; 424—second opening; 425—third opening;
51—hanging plate; 511—hook; 52—control panel; 53—negative ion generator; 530—emitting head; 531—negative ion releasing brush; 532—support; and 533—guide plate.

DETAILED DESCRIPTION

In order to clarify the technical problems, technical solutions, and beneficial effects to be solved by this application, the following further describes this application in detail with reference to the accompanying drawings and embodiments. It should be understood that the specific embodiments described here are only used to explain the application, and not used to limit the application.

It should be noted that when an element is referred to as being "fixed to" or "provided on" another element, it can be directly or indirectly on the other element. When an element is described to be "connected to" another element, it can be directly or indirectly connected to the other element.

In addition, the terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of the present application, the phrase "a plurality of" means two or more than two, unless otherwise specifically defined. "Several" means one or more than one, unless otherwise specifically defined.

In the description of this application, it should be understood that the orientation or positional relationship indicated by the terms "center", "length", "width", "thickness", "upper", "lower", "front", "rear", "left", "right", "vertical", "horizontal", "top", "bottom", "inner", "outer", etc. are based on the orientation or positional relationship shown in the drawings, and are only for conveniently describing this application and simplifying the description, rather than indicating or implying that the device or element referred to must have a specific orientation, be constructed and operated in a specific orientation, and therefore cannot be understood as a limitation of the application.

In the description of this application, it should be noted that the terms "mount", "connect", and "communicate" should be understood in a broad sense, unless otherwise clearly specified and limited. For example, it can be a fixed connection, a detachable connection or integrally connected; it can be a mechanical connection or an electrical connection; it can be a direct connection or indirect connection through an intermediate medium, and it can be an internal communication between two components or the interaction between two components. For those skilled in the art, the specific meanings of the above-mentioned terms in this application can be understood according to specific circumstances.

References described in the specification of this application to "one embodiment", "some embodiments" or "embodiments" mean that one or more embodiments of the present application include a specific feature, structure, or characteristic described in conjunction with the embodiments. Therefore, the phases "in one embodiment", "in some embodiments", "in other embodiments", "in some other embodiments", etc. appearing in different places in this specification are not necessarily all refer to the same embodiment, but mean "one or more but not all embodiments", unless otherwise specifically emphasized. In addition, in one or more embodiments, specific features, structures, or characteristics may be combined in any suitable manner.

The English original texts corresponding to the English abbreviations used in this application are as follows:
LED: Light Emitting Diode.

Figure 5:
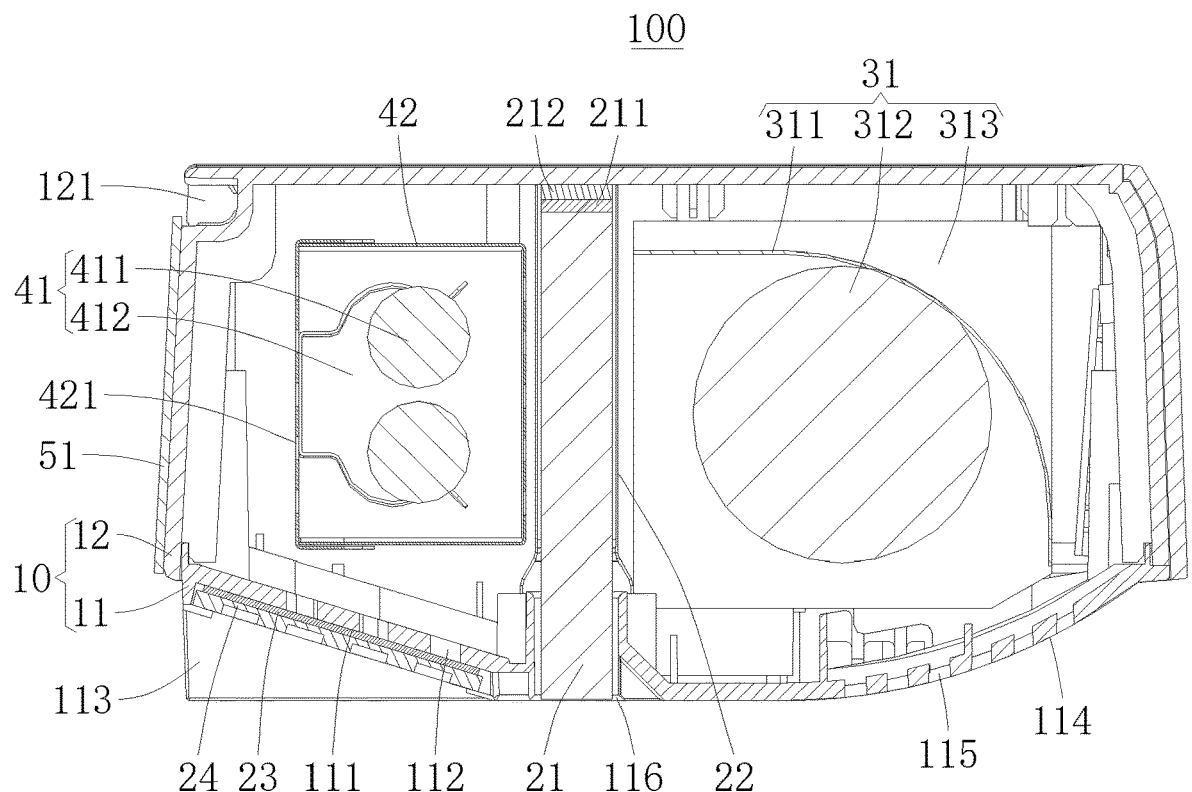
FIG. 5 is a schematic sectional view of the wall-mounted air purifier in FIG. 4.

For the convenience of description, referring to FIGS. 1 and 5, it is defined in this application that: when the casing 10 is mounted on a wall, a side of the casing 10 close to the wall is rear side of the casing 10 and the wall-mounted air purifier 100, and the side far away from the wall is the front side of the casing 10 and the wall-mounted air purifier 100.

Figure 2:
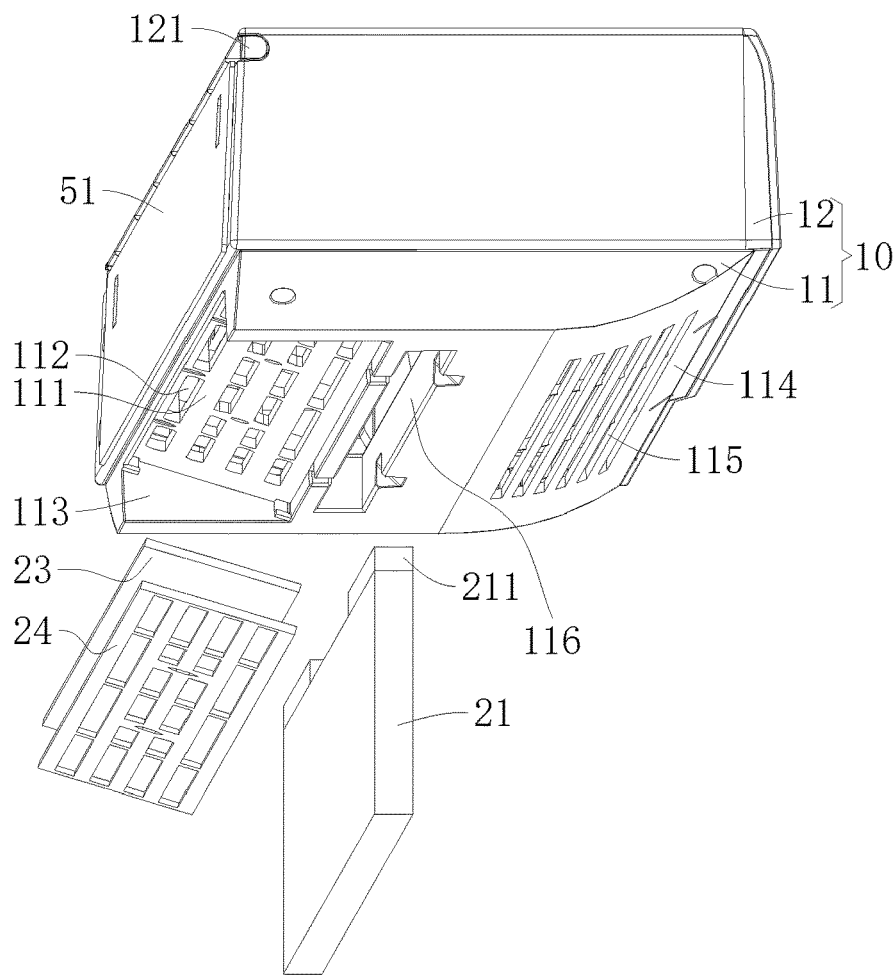
FIG. 2 is a schematic structural view of the filter and the removed filter mesh in the wall-mounted air purifier of FIG. 1.
Figure 3:
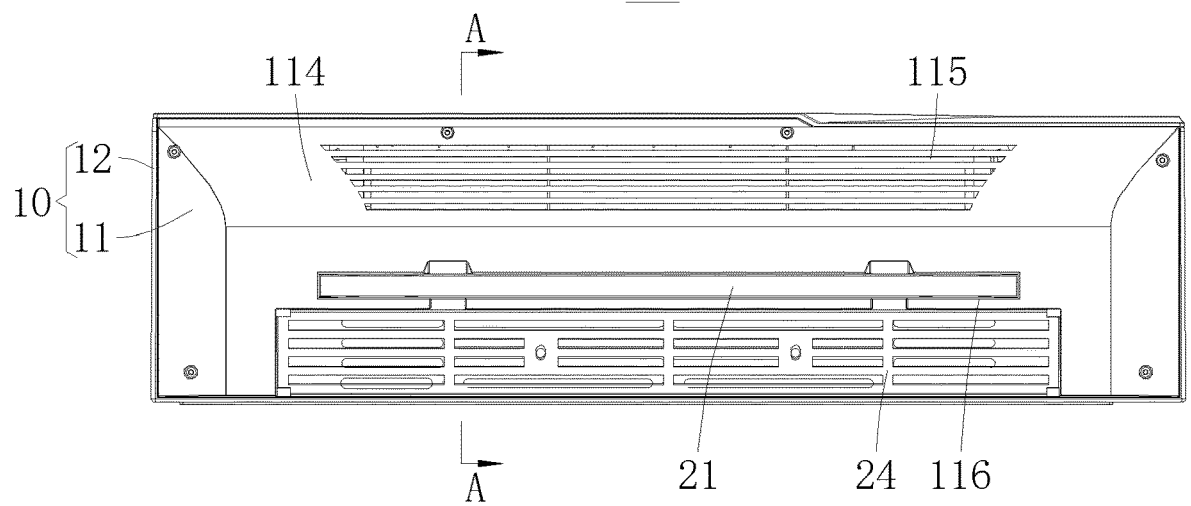
FIG. 3 is a schematic bottom view of the wall-mounted air purifier of FIG. 1.
Figure 4:
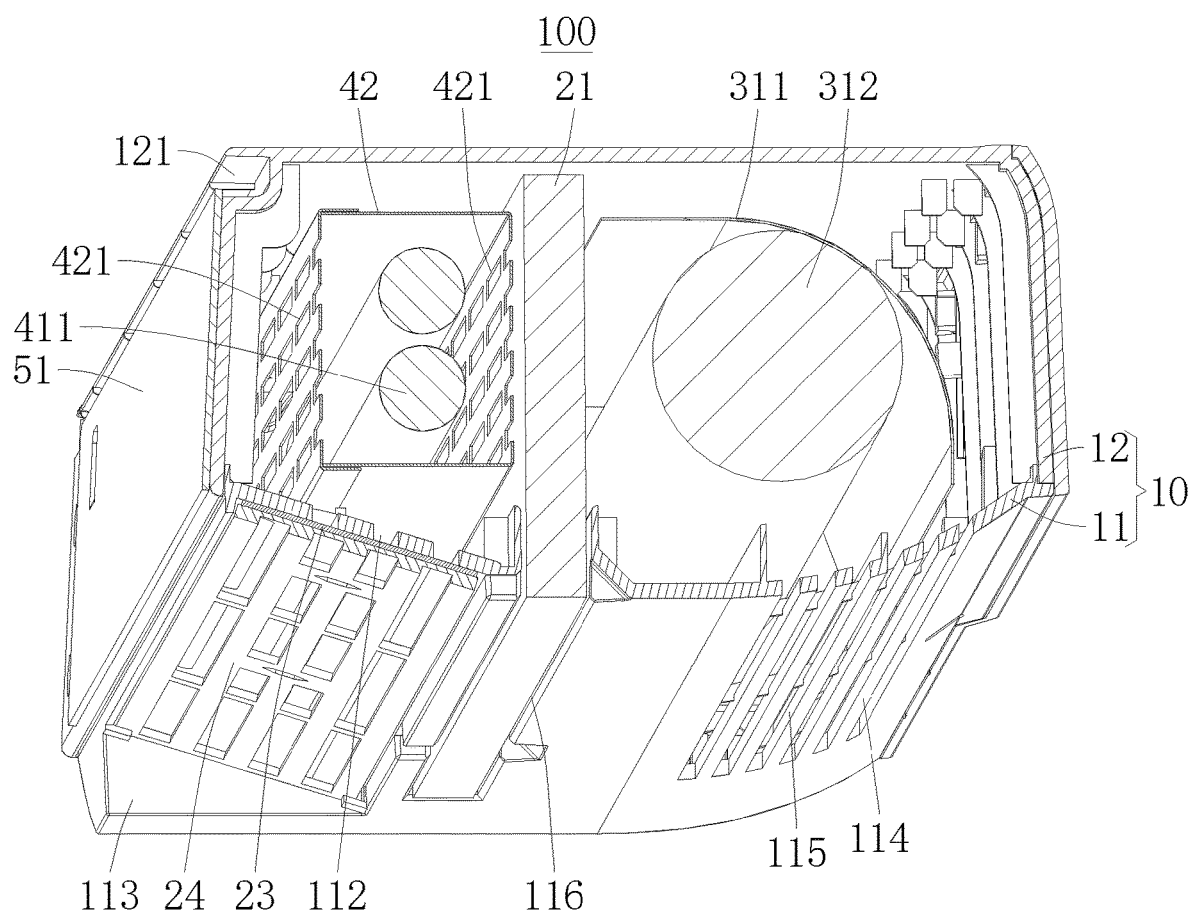
FIG. 4 is a perspective sectional view of the structure along the line A-A in FIG. 3.

Referring to FIGS. 1 to 5, FIG. 1 is a schematic view of the three-dimensional structure of the wall-mounted air purifier 100 of this embodiment. FIG. 2 is a schematic structural view when the filter 21 and the filter mesh 23 of the wall-mounted air purifier 100 of this embodiment are separated from the casing 10. FIG. 3 is a schematic bottom view of the wall-mounted air purifier 100 of this embodiment. FIG. 4 is a schematic cross-sectional structure view taken along A-A in FIG. 3, and FIG. 4 is a cut-away perspective view of the wall-mounted air purifier 100. FIG. 5 is a schematic sectional view of the structure taken along A-A in FIG. 3.

Referring to FIGS. 4 and 5, the wall-mounted air purifier 100 provided in the present application will now be described. The wall-mounted air purifier 100 includes a casing 10, a filter 21 and a fan 31; the filter 21 and the fan 31 are mounted in the casing 10, and the filter 21 and the fan 31 are supported and protected by the casing 10. The casing 10 is provided with an air inlet 112 and an air outlet 115. The air outlet 115 is located at a position corresponding to the outlet of the fan 31, and the filter 21 is located between the air inlet 112 and the fan 31, so that when the fan 31 works, the air entering the casing 10 from the air inlet 112, is filtered and purified by the filter 21, and then blown out from the air outlet 115 by the fan 31 to achieve air purification. In addition, the filter 21 is arranged between the air inlet 112 and the fan 31 so that the air will be filtered and purified by the filter 21 before entering the fan 31, thereby reducing the impurities adhered to the fan 31.

Referring to FIGS. 4 and 5, the wall-mounted air purifier 100 further includes an ultraviolet light source 41; the ultraviolet light source 41 is mounted in the casing 10, and the ultraviolet light source 41 is supported and protected by the casing 10. The ultraviolet light source 41 is arranged between the air inlet 112 and the fan 31, so that the air is sterilized by the ultraviolet light source 41 before entering the fan 31, to improve the air purification function and provide cleaner air.

Compared with the prior art, the wall-mounted air purifier 100 provided in the present application filters and purifies the air by arranging a filter 21 in the casing 10; and the ultraviolet light source 41 is mounted in the casing 10 to sterilize the gas entering the air inlet 112 and purify the air and improve the air purification ability.

In one embodiment, referring to FIGS. 1 and 5, the air inlet 112 on the casing 10 is located at a corresponding position on the rear side of the bottom of the casing 10. Since the wall-mounted air purifier 100 is generally mounted on a wall, the air inlet 112 is provided at the bottom of the casing 10, so that the air under the wall-mounted air purifier 100 can be directly sucked and purified, and the air in the activity area of user is purified more quickly, and the purified air can be improved for users. When the air inlet 112 is arranged at the corresponding position on the rear side of the bottom of the casing 10, the wall can guide and gather the air entering the air inlet 112, so that the air under the casing 10 circulates upwards into the casing 10 and improves the air purification ability. Besides, it can better prevent impurities from falling into the air inlet 112. It can be understood that in one embodiment, the air inlet 112 may also be provided on the top surface of the casing 10.

In one embodiment, referring to FIGS. 2 and 4, the bottom of the casing 10 has an inclined surface 111, the air inlet 112 is provided on the inclined surface 111, and the inclined surface 111 extends backward and upward from the bottom of the casing 10 obliquely. The inclined surface 111 is provided, and the air inlet 112 is arranged on the inclined surface 111. When the casing 10 is mounted on the wall, the inclined surface 111 and the wall can form a horn-like shape, i.e., a trough body structure which is open in the lower side and gathered in the upper side, which can better gather air and facilitate the gas to enter the air inlet 112 more quickly, so that the air under the casing 10 circulates upwards into the casing 10 to improve the air purification ability.

In one embodiment, the inclined surface 111 is flat, which is easy for processing. It should be understood that the inclined surface 111 can also be provided to be arc-shaped or curved.

In one embodiment, the bottom of the casing 10 is provided with baffles 113 protruding downwards at both ends of the inclined surface 111, so that it can better cooperate with the wall to form a cavity with a reduced area from bottom to top for better air gathering, and the air can enter the air inlet 112 more quickly, so that the air under the casing 10 circulates upward into the casing 10, and the air purification ability is improved.

In one embodiment, referring to FIGS. 4 and 5, the filter 21 may be a primary filter, a high efficiency filter, an activated carbon filter, or the like.

In one embodiment, referring to FIGS. 2, 4, and 5, the wall-mounted air purifier 100 further includes a filter mesh 23. The filter mesh 23 is detachably mounted on the casing 10, and the filter mesh 23 covers the air inlet 112, to filter the air through the filter 23, reduce dust, hair and other impurities entering the casing 10. The filter mesh 23 can be detachably mounted on the casing 10 for disassembly, cleaning or replacement.

In one embodiment, the wall-mounted air purifier 100 further includes a grille plate 24, which is detachably mounted on the casing 10, and the grille plate 24 is used to support the filter mesh 23. The grille plate 24 is provided to support the filter mesh 23 so as to facilitate the installation of the filter mesh 23 on the casing 10.

In one embodiment, the grille plate 24 may be fixed on the casing 10 by screws to facilitate disassembly. It can be understood that the grille plate 24 can also be clamped on the casing 10.

In one embodiment, the filter mesh 23 can be made as a whole with the grille plate 24, that is, the filter mesh 23 and the grille plate 24 are an integral structure and the filter mesh 23 is supported through the grille plate 24, so that filter mesh 23 is mounted on the casing 10. It can be understood that in some embodiments, the filter mesh 23 can be separately provided, and the filter mesh 23 can be directly fixed on the casing 10. For example, the filter mesh 23 can be fixed on the casing 10 by screw, magnetic force, snap, etc. This structure can reduce the cost, and facilitate the cleaning of the filter mesh 23 after disassembly.

In one embodiment, the air outlet 115 on the casing 10 is provided at a corresponding position on the front side of the bottom of the casing 10, so that the air in the area below the casing 10 can be blown better, so as to better purify the air. It can also enable users under the wall-mounted air purifier 100 to get the purified air faster, and improve user experience.

In one embodiment, the bottom of the casing 10 has an air outlet surface 114, the air outlet 115 is provided on the air outlet surface 114, and the air outlet surface 114 extends forward and upward from the bottom of the casing 10, so that the air blown out by the air outlet 115 is blown to the lower front side of the wall-mounted air purifier 100, which is beneficial for the air flowing under the wall-mounted air purifier 100, and the purified air can directly cover a larger area so that the user can get the purified air faster, improving the user experience.

In one embodiment, the air outlet surface 114 is arc-shaped to reduce the edges and corners on the front side of the bottom of the casing 10, improving safety and aesthetics, and also making the air blown from the air outlet 115 cover a larger area. It can be understood that the air outlet surface 114 can also be inclined for processing purpose.

In one embodiment, the casing 10 includes a bottom casing 11 and a housing shell 12 covering the bottom casing 11, so it is convenient for processing and manufacturing. It can be understood that in other embodiments, the casing 10 can also be formed by combining multiple plates.

In one embodiment, when the air inlet 112 is provided at the bottom of the casing 10, the corresponding air inlet 112 is provided on the bottom casing 11. Similarly, when the air outlet 115 is provided at the bottom of the casing 10, the air outlet 115 can be provided on the bottom casing 11. It can be understood that when the air inlet 112 is provided on the top of the casing 10, the corresponding air inlet 112 is provided on the housing shell 12.

In one embodiment, referring to FIG. 1, the front side of the casing 10 is provided with a control panel 52. The control panel 52 is inclined from top to bottom toward the rear side of the casing 10 to facilitate user operations and user convenience for determining the location of the control panel 52. In one embodiment, the control panel 52 is provided on the housing shell 12, so that it is convenient for processing and manufacturing.

Figure 6:
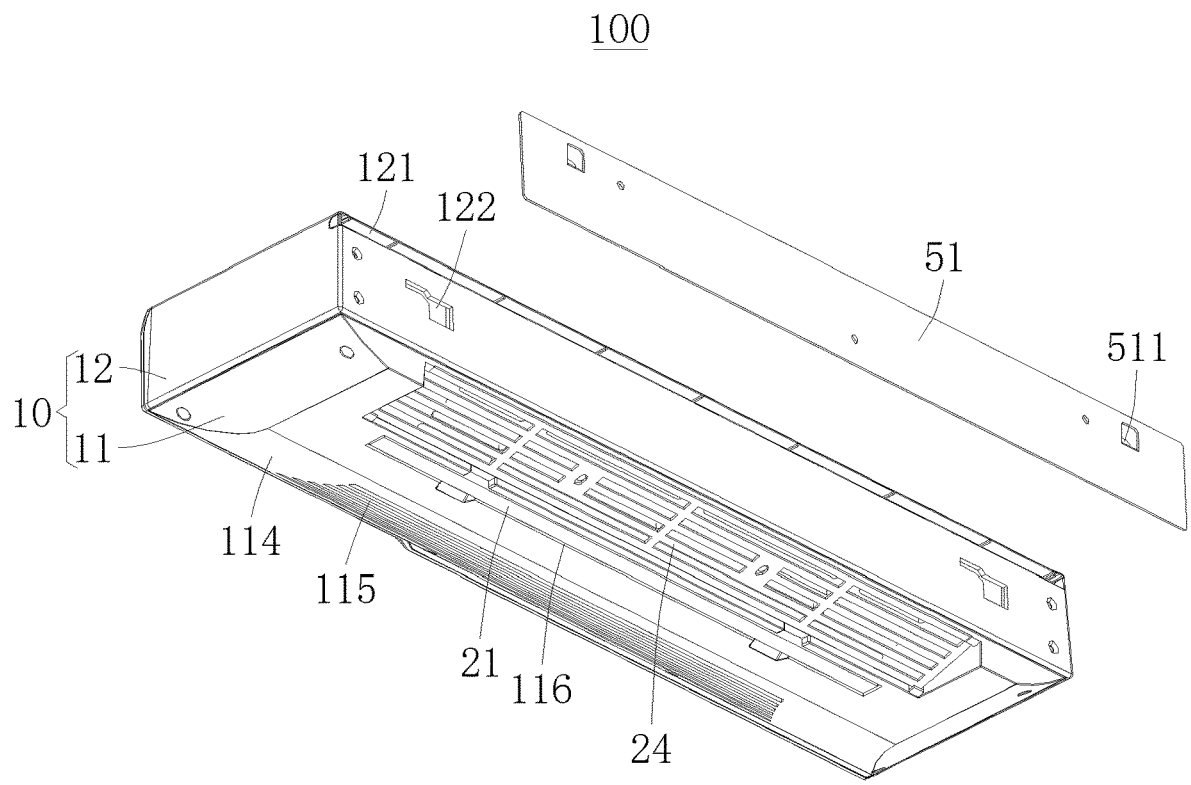
FIG. 6 is a schematic structural view of the wall-mounted air purifier of FIG. 1 when it is separated with the hanging plates.

In one embodiment, referring to FIG. 6, it is a schematic structural view of the wall-mounted air purifier 100 of this embodiment when the hanging plate 51 is separated from the casing 10. A hanging snap 122 is provided on the rear side of the casing 10 so that the casing 10 can be mounted on a wall by hooking, which is convenient for installation and fixation. It can be understood that in some other embodiments, screws may also be used to install the casing 10 on the wall.

In one embodiment, referring to FIG. 6, the wall-mounted air purifier 100 further includes a hanging plate 51. The hanging plate 51 is provided with a hook 511 that cooperates with the hanging snap 122, and the hanging plate 51 is used to be fixed on the wall. The hanging plate 51 can be fixed on the wall first, and then the casing 10 can be hung on the hanging plate 51, which is convenient for positioning and installation. The hanging plate 51 can be pasted on the wall or fixed on the wall by spikes.

In one embodiment, referring to FIG. 6, a wire concealing groove 121 is provided on the rear side of the casing 10 so that the power supply can be placed in the wire concealing groove 121 to facilitate wiring.

Figure 7:
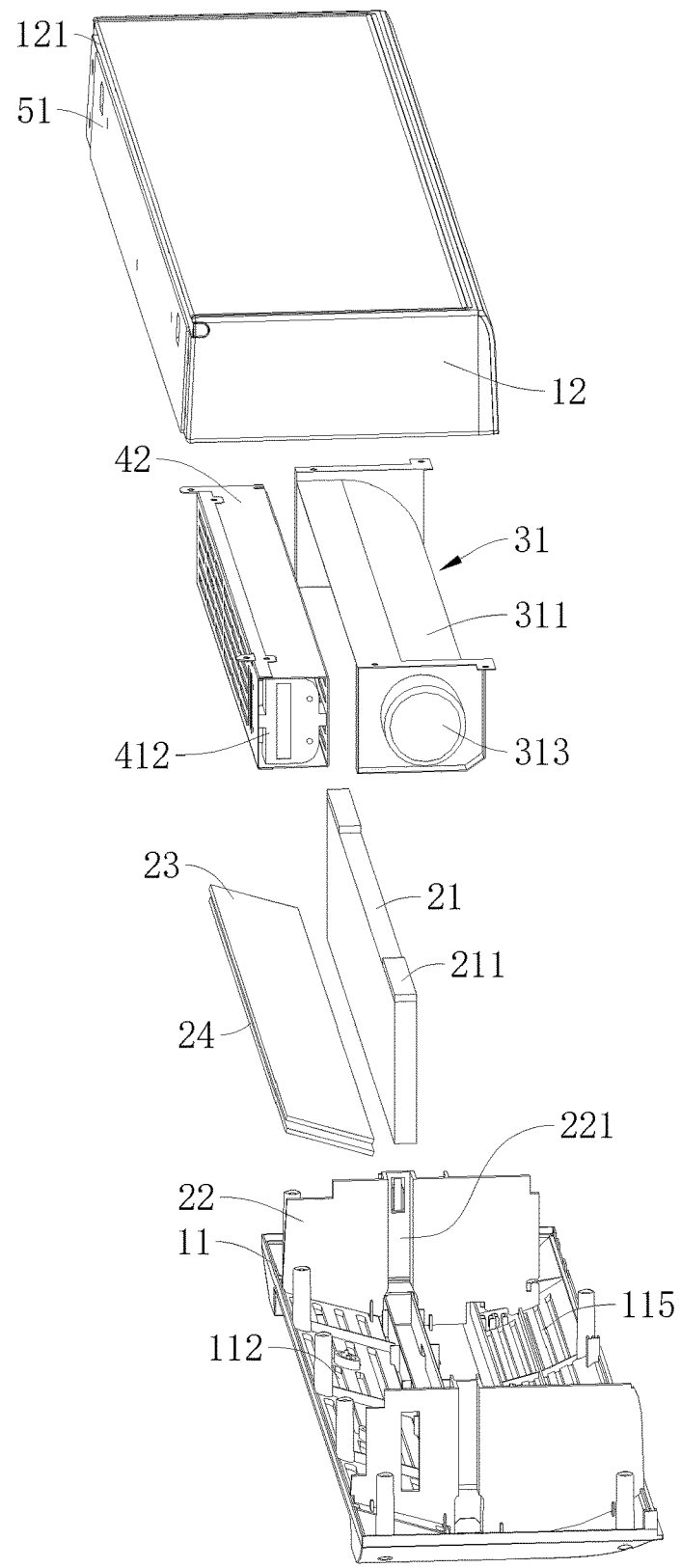
FIG. 7 is a first schematic view of an exploded structure of the wall-mounted air purifier of FIG. 1.
Figure 8:
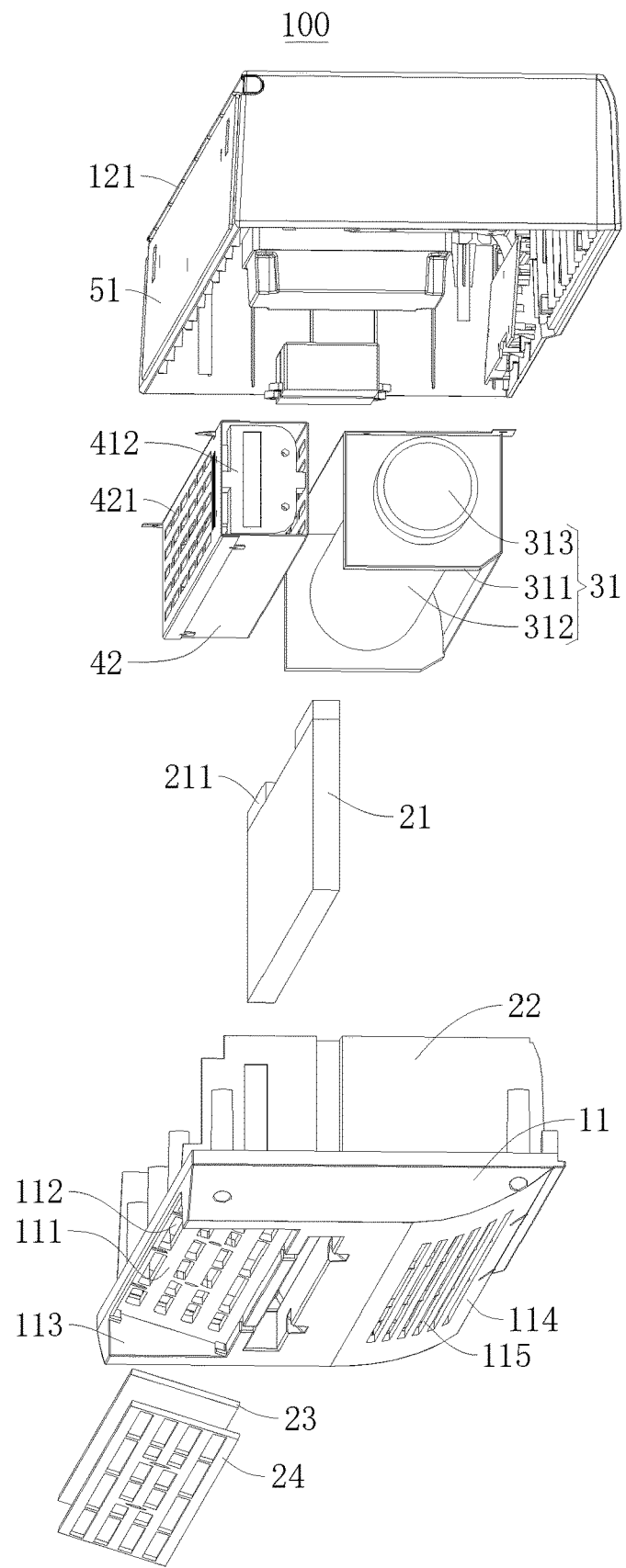
FIG. 8 is a second schematic view of an exploded structure of the wall-mounted air purifier of FIG. 1.

Referring to FIGS. 7 and 8. FIG. 7 is an exploded structural view of the wall-mounted air purifier 100 of this embodiment from a certain angle. FIG. 8 is an exploded structure view of the wall-mounted air purifier 100 of this embodiment from another angle.

In one embodiment, referring to FIGS. 2, 7 and 8, the casing 10 is provided with a socket 116, which is used for plugging and unplugging the filter 21, and the filter 21 is detachably inserted into the casing 10 through the socket 116, the filter 21 can be inserted from the socket 116 into the casing 10 to facilitate the installation of the filter 21; It can be understood that the filter 21 can also be removed from the socket 116 for cleaning or replacement of the filter 21. It can be understood that in other embodiments, the casing 10 can also be removed to disassemble the filter 21.

In one embodiment, the socket 116 is provided on the bottom surface of the casing 10. Since the wall-mounted air purifier 100 is fixed on the wall when in use, a socket 116 is provided on the bottom surface of the casing 10 to facilitate the insertion and removal of the filter 21 from the socket 116, and facilitate the disassembly and replacement of the filter 21. It can be understood that in other embodiments, a socket 116 can also be provided on the side of the casing 10 to insert and remove the filter 21 from the side of the casing 10.

In one embodiment, the filter 21 is vertically arranged in the casing 10 to facilitate the insertion and removal of the filter 21 into and from the socket 116, respectively. In addition, the space occupied by the filter 21 in the front and rear direction of the casing 10 is reduced.

In one embodiment, a magnetic member 212 is provided in the casing 10, a magnetic block 211 is provided on the filter 21, and the magnetic member 212 is connected to the magnetic block 211 with magnetic attraction, thereby magnetically fixing the filter 21 in the casing 10, to facilitate the disassembly and assembly of the filter 21.

In one embodiment, the magnetic member 212 is a magnet, and the magnetic block 211 may be a magnet with magnetic force, such as a magnet matched with the magnetic member 212 for magnetic attraction. It can be understood that the magnetic member 212 may also be a soft magnet such as an iron block. It can be understood that the magnetic block 211 is a magnet, and the magnetic member 212 may be a magnet with magnetic force, such as a magnet matched with the magnetic block 211 for magnetic attraction. It can be understood that the magnetic block 211 may also be a soft magnet such as an iron block.

In one embodiment, a snap may be provided in the casing 10 to clamp the filter 21 in the casing 10, which may also facilitate the disassembly and assembly of the filter 21.

In one embodiment, referring to FIGS. 7 and 8, two separators 22 are provided in the casing 10, and the two separators 22 are respectively located at both ends of the filter 21, and the separator 22 is provided with sliding grooves 221, so that when the filter 21 is disassembled and assembled, the sliding grooves 221 can act as a guide, and when the filter 21 is installed in the casing 10, the filter 21 can be positioned by the sliding grooves 221. In addition, the separator 22 is provided to allow all the air entering the casing 10 to pass through the filter 21 to purify the air. In addition, the provision of the separator 22 can also increase the strength of the casing 10.

In one embodiment, the air inlet 112 and the fan 31 are located between the two separators 22, so that the air entering from the air inlet 112 can be purified and filtered by the filter 21 to ensure the air purification effect.

In one embodiment, referring to FIGS. 5, 7 and 8, the fan 31 includes a wind hood 311, a tubular wind wheel 312, and a motor 313. The tubular wind wheel 312 is connected to and driven to rotate by the motor 313. The tubular wind wheel 312 is installed in the wind hood 311, and the airflow is guided by the wind hood 311. By using the tubular wind wheel 312, the volume can be smaller and the air volume can be large, so that the casing 10 can be smaller. It can be understood that in some other embodiments, other structures of fan 31 can also be used.

In one embodiment, referring to FIGS. 4, 5 and 7, a light shield 42 is further provided in the casing 10, and covered on the ultraviolet light source 41. The ultraviolet light beam emitted by the ultraviolet light source 41 is constrained in a certain space by providing the light shield 42 to increase the intensity of the ultraviolet light in the space, so that the ultraviolet light can disinfect the air in the space and improve the effect of ultraviolet light disinfection.

In one embodiment, the ultraviolet light source 41 is arranged between the air inlet 112 and the filter 21, so that before the air enters the filter 21, it will be irradiated and sterilized by ultraviolet light to better kill bacteria in the air and prevent bacteria and other organisms growing in the filter 21 and protect the filter 21 to a certain extent.

In one embodiment, the light shield 42 shields the side of the ultraviolet light source 41 close to the air inlet 112, so as to prevent the ultraviolet light emitted by the ultraviolet light source 41 from leaking from the air inlet 112 and improve safety.

In one embodiment, referring to FIGS. 4, 5 and 8, the light shield 42 surrounds the ultraviolet light source 41, and the front and rear sides of the light shield 42 are respectively provided with vents 421, which can better prevent ultraviolet light from leakage from the air inlet 112, improving safety, and can gather the ultraviolet light emitted by the ultraviolet light source 41 in the light shield 42 to sterilize the air passing through the light shield 42.

In one embodiment, the light shield 42 adopts two covers with U-shaped cross section which is fastened with each other to surround the ultraviolet light source 41. This is convenient for manufacturing. It can be understood that the light shield 42 can also be a cylindrical cover, and the ultraviolet light source 41 is directly supported in the light shield 42.

In one embodiment, the ultraviolet light source 41 includes an ultraviolet lamp tube 411 and a lamp holder 412. The lamp holder 412 is installed in the casing 10 and protected by the casing 10. The ultraviolet lamp tube 411 is installed on the lamp holder 412, and the ultraviolet lamp tube 411 is supported by the lamp holder 412, and power is supplied to the ultraviolet lamp tube 411, so that the ultraviolet lamp tube 411 can emit ultraviolet light. Using the ultraviolet lamp 411 will reduce coat, and the light emission is more uniform.

In one embodiment, the ultraviolet lamp tube 411 can be detachably installed on the lamp holder 412, which is convenient for replacing the ultraviolet lamp tube 411 and maintaining.

In one embodiment, the inner surface of the light shield 42 is provided with a reflective layer, to reflect the ultraviolet light emitted by the ultraviolet light source 41 to the limited space, so as to disinfect and purify the air in the space.

Figure 9:
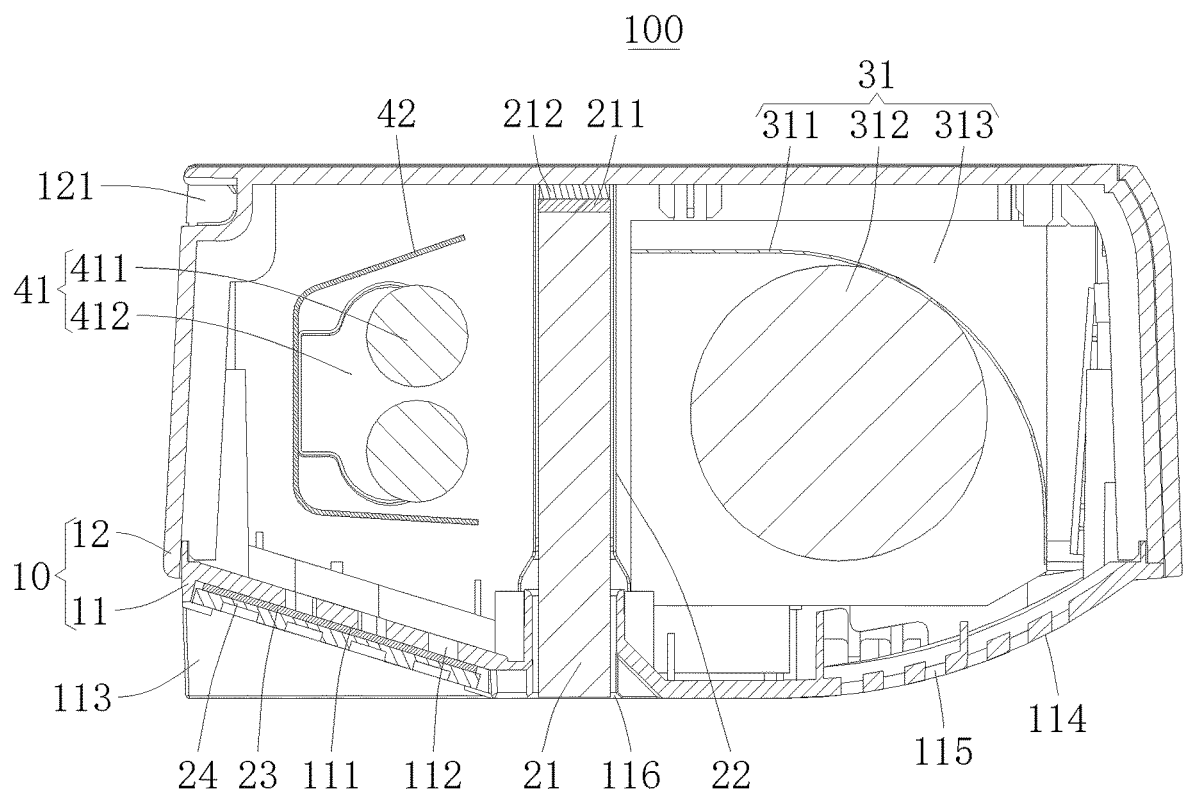
FIG. 9 is a schematic cross-sectional structure view of a wall-mounted air purifier provided in Embodiment 2 of the application.

In one embodiment, referring to FIG. 9, it is a schematic cross-sectional structure view of the wall-mounted air purifier 100 of this embodiment. The side of the light shield 42 close to the filter 21 is open. This structure can not only sterilize the air passing through the filter 21, but also sterilize the filter 21, and reduce the bacteria growth on the filter 21, enhance the air purification effect.

In one embodiment, the light shield 42 may use a cover with a U-shaped cross section, which has a simple structure, is convenient for processing and manufacturing, is cost-efficient, and is convenient for installation.

In one embodiment, the ultraviolet light source 41 is located on the side of the filter 21 close to the air inlet 112, the side of the light shield 42 close to the filter 21 is open, and the side of the light shield 42 can also block the side of the ultraviolet light source 41 close to the air inlet 112 to prevent ultraviolet light leaking from the air inlet 112.

Figure 10:
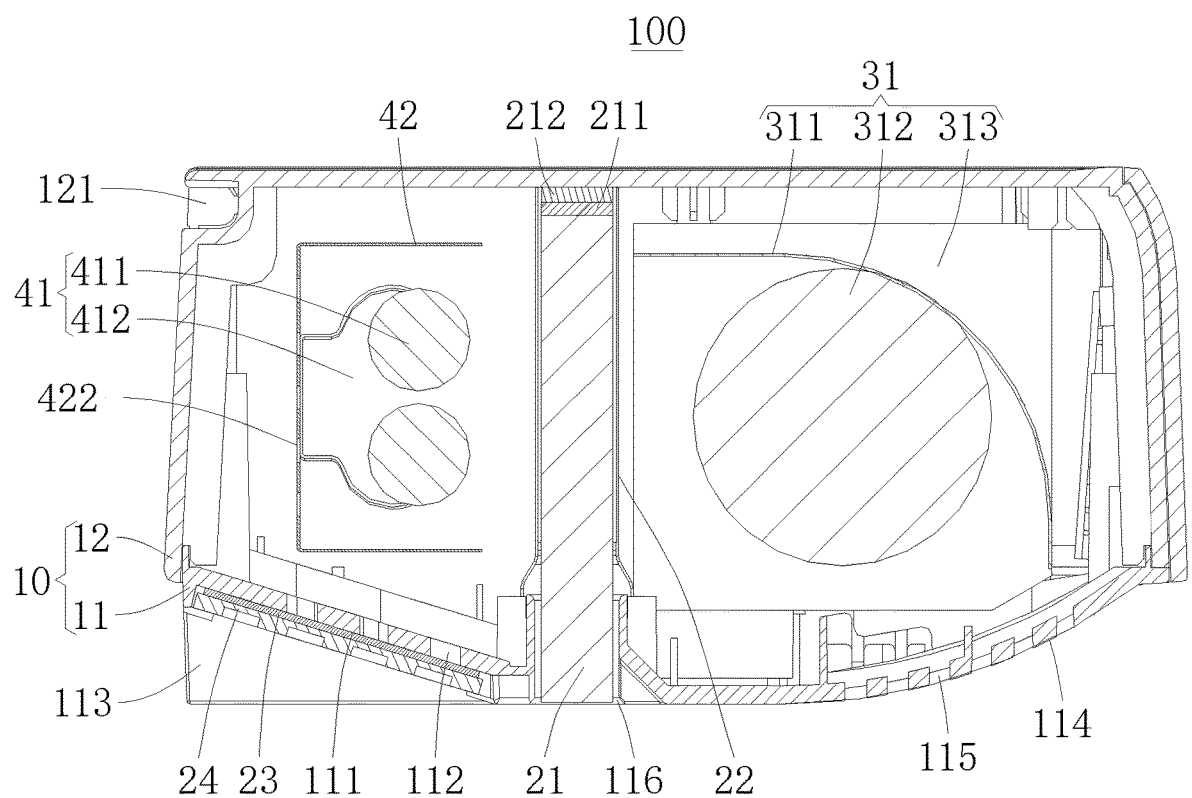
FIG. 10 is a schematic cross-sectional structure view of a wall-mounted air purifier provided in Embodiment 3 of the application.

In one embodiment, referring to FIG. 10, it is a cross-sectional structural view of the wall-mounted air purifier 100 of this embodiment. In this embodiment, the other side of the light shield 42 is provided with a first opening 422, that is, the side of the light shield 42 away from the filter 21 is provided with a first opening 422, so that air can pass through the first opening 422 and flow to the filter 21 to reduce the resistance to the air and improve the air purification ability.

Figure 11:
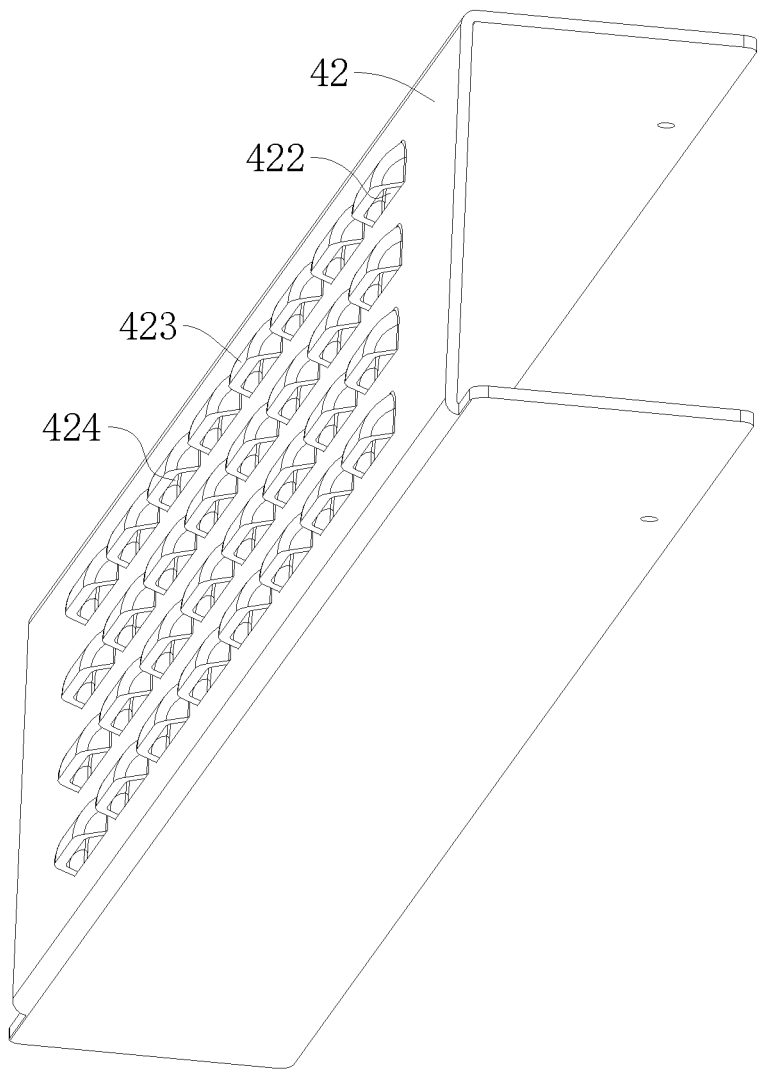
FIG. 11 is a schematic structural view of a light shield in a wall-mounted air purifier provided in Embodiment 4 of the application.

In one embodiment, referring to FIG. 11, it is a schematic structural view of the light shield 42 of this embodiment. The light shield 42 is provided with a blocking piece 423 which blocks the first opening 422, and a second opening 424 communicating with the first opening 422 is formed between the blocking piece 423 and the light shield 42. The blocking piece 423 is provided to cover the first opening 422, which can better prevent leakage of the ultraviolet light source 41 and improve safety.

Figure 12:
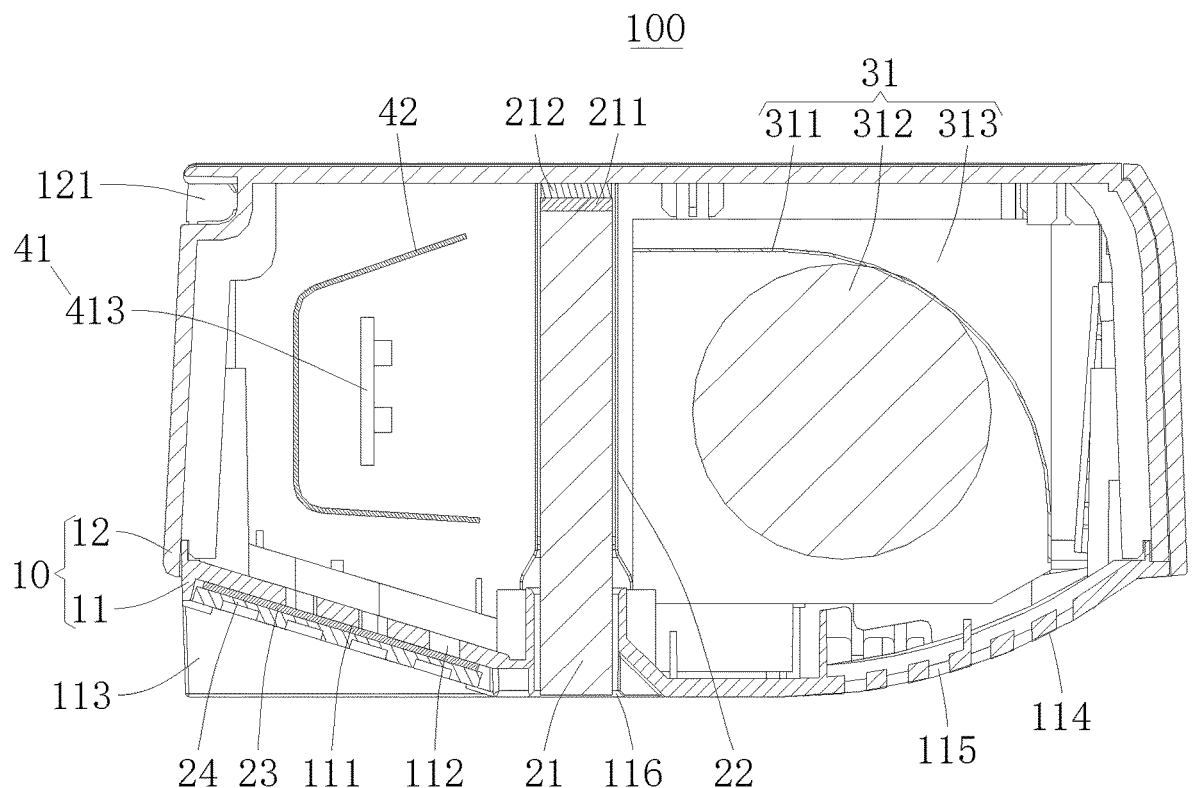
FIG. 12 is a schematic cross-sectional structure view of a wall-mounted air purifier provided in Embodiment 5 of the application.

In one embodiment, referring to FIG. 12, it is a cross-sectional structure view of the wall-mounted air purifier 100 of this embodiment. In this embodiment, the ultraviolet light source 41 includes an ultraviolet LED module 413, and the ultraviolet LED module 413 is installed in the casing 10. The use of UV LED module 413 is more energy-efficient and has a longer life.

Figure 13:
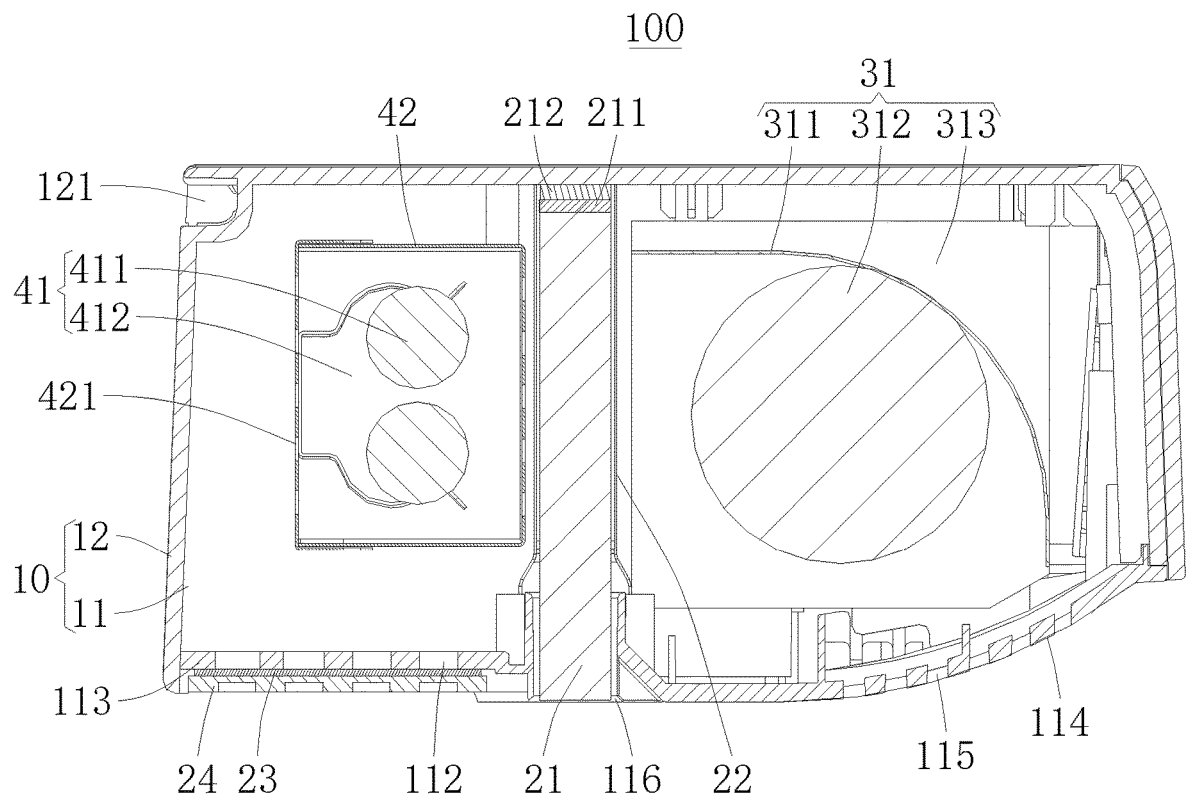
FIG. 13 is a schematic cross-sectional structure view of a wall-mounted air purifier provided in Embodiment 6 of the application.

In one embodiment, referring to FIG. 13, it is a schematic cross-sectional view of the wall-mounted air purifier 100 of this embodiment. In this embodiment, the rear side of the bottom of the casing 10 is flat, and the air inlet 112 is located on the rear side of the bottom of the casing 10. The structure is easy to manufacture.

Figure 14:
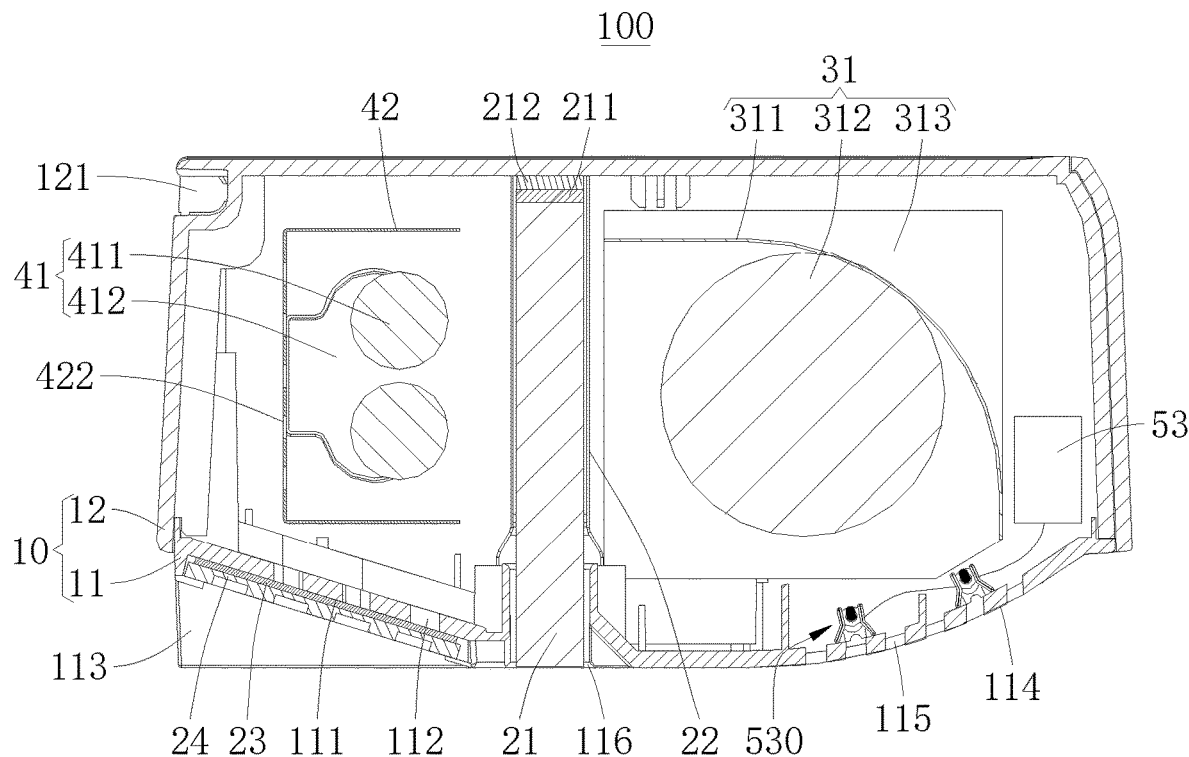
FIG. 14 is a schematic cross-sectional structure view of a wall-mounted air purifier provided in Embodiment 7 of the application.
Figure 15:
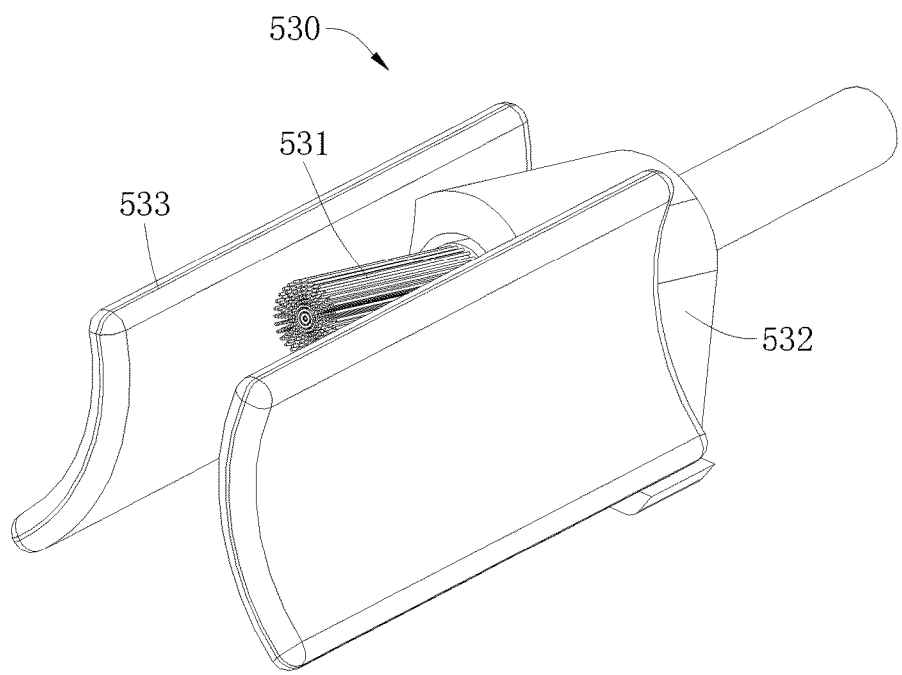
FIG. 15 is a schematic view of an enlarged structure of the emitting head in FIG. 14.

In one embodiment, referring to FIG. 14 and FIG. 15. FIG. 14 is a schematic cross-sectional view of the wall-mounted air purifier 100 of this embodiment. FIG. 15 is a schematic structural view of the emitting head of this embodiment. In this embodiment, the wall-mounted air purifier 100 further includes a negative ion generator 53. The negative ion generator 53 has an emitting head 530. The emitting head 530 of the negative ion generator 53 is arranged at the corresponding position of the air outlet 115, so that the airflow generated by the fan 31 passes through the emitting head 530 of the negative ion generator 53, before it flows out of the air outlet 115, to form an airflow with negative ions which can better disinfect and purify the air.

In one embodiment, the emitting head 530 includes a negative ion releasing brush 531, a support 532 and two guide plates 533. The support 532 is mounted on the casing 10, the negative ion releasing brush 531 is mounted on the support 532, the negative ion releasing brush 531 is supported by the support 532, and the negative ion releasing brush 531 is extended to the air outlet 115, two guide plates 533 are respectively arranged on opposite sides of the negative ion releasing brush 531. The distance between the two guide plates 533 is gradually expanded from the middle of the guide plate 533 downward, that is, the distance between the two guide plates 533 is gradually expanded from the middle of the guide plates 533 to the lower side of the guide plate 533, so that the space between the lower parts of the two guide plates 533 gradually increases, so the airflow will diffuse with a reducing speed when it flows to the lower part of the two guide plates 533, thereby making the negative ions in the airflow better diffuse and increasing the area covered by the negative ions.

In one embodiment, the guide plate 533 is fixedly connected to the support 532 to facilitate the installation and fixation of the guide plate 533, and further facilitate the installation and fixation of the emitting head 530. It can be understood that in some embodiments, the guide plate 533 may be separately supported in the casing 10.

In one embodiment, the distance between the two guide plates 533 is gradually expanded upward from the middle of the guide plate 533, that is, the distance between the two guide plates 533 is gradually expanded from the middle of the guide plate 533 to the upper side of the guide plate 533, so that more air enters between the two guide plates 533, and more air contacts the negative ion releasing brush 531, thereby generating more negative ions.

In one embodiment, the distance between the upper sides of the two guide plates 533 is less than the distance between the lower sides of the two guide plates 533, so as to ensure that the airflow velocity from the lower sides of the two guide plates 533 is less than that outside the two guide plates 533, which will form a certain siphon effect on the lower side of the two guide plates 533 to better diffuse the negative ions in the air flow out between the two guide plates 533, thereby increasing the coverage area of negative ions.

In one embodiment, the negative ion releasing brush 531 is located at a corresponding position above the middle of the guide plate 533, so that more airflow passes through the negative ion releasing brush 531, and then is guided and diffused by the guide plate 533.

In one embodiment, the negative ion releasing brush 531 extends obliquely upward, that is, the negative ion releasing brush 531 extends obliquely upward from the support 532 to the free end of the negative ion releasing brush 531. Since the free end of the negative ion releasing brush 531 is relatively more open, the negative ion releasing brush 531 is extended obliquely upwards, which can reduce the resistance of the negative ion releasing brush 531 to the air flow, thereby facilitating the air flow through the negative ion releasing brush 531 to produce more negative ions.

Figure 16:
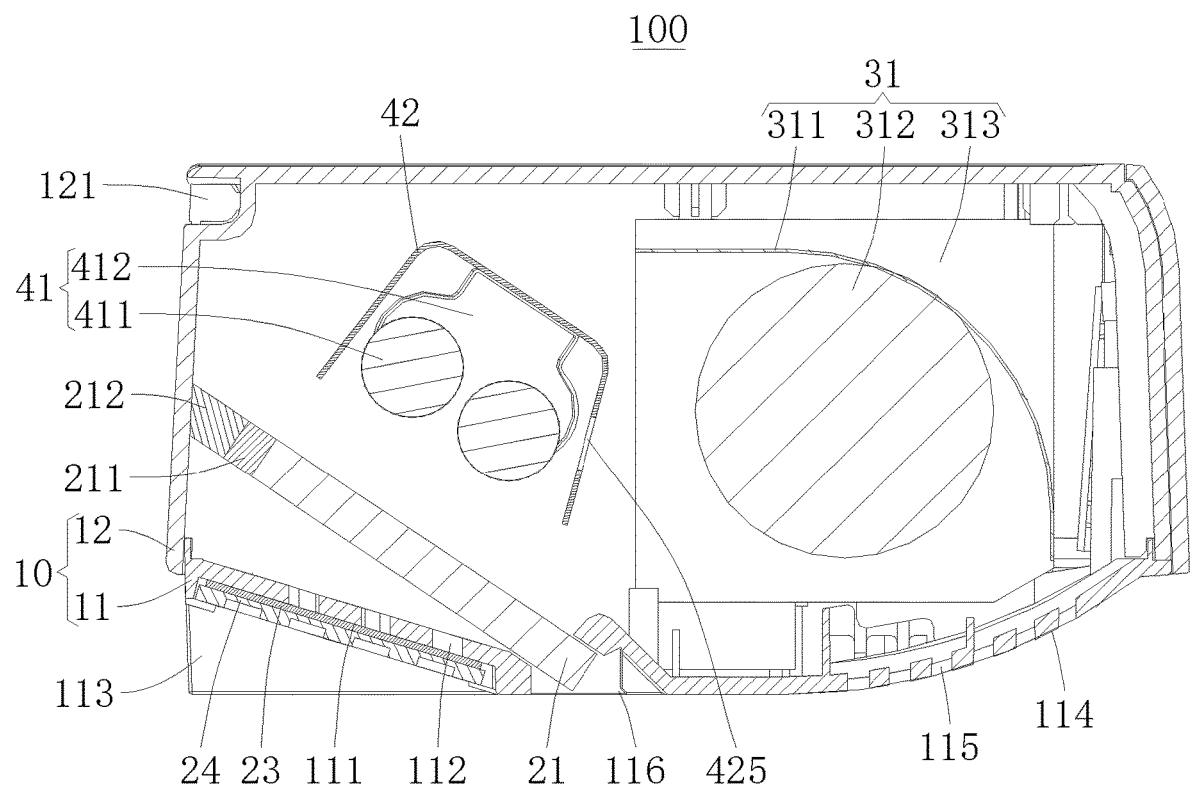
FIG. 16 is a schematic cross-sectional structure view of a wall-mounted air purifier provided in Embodiment 8 of the application.

In one embodiment, referring to FIG. 16, it is a schematic cross-sectional view of the wall-mounted air purifier 100 of this embodiment. In this embodiment, the ultraviolet light source 41 is arranged between the fan 31 and the filter 21, and the air purified by the filter 21 is filtered and then irradiated and sterilized by the ultraviolet light source 41 to ensure the purification effect of the air. In addition, the ultraviolet light source 41 is arranged between the fan 31 and the filter 21, and the filter 21 can also be used to block the ultraviolet light to prevent the ultraviolet light from leaking from the air inlet 112.

In one embodiment, referring to FIG. 16, the light shield 42 is provided with a third opening 425, so that after the air is filtered by the filter 21, the air entering the light shield 42 can better flow to the fan 31 and reduce the resistance to air.

Figure 17:
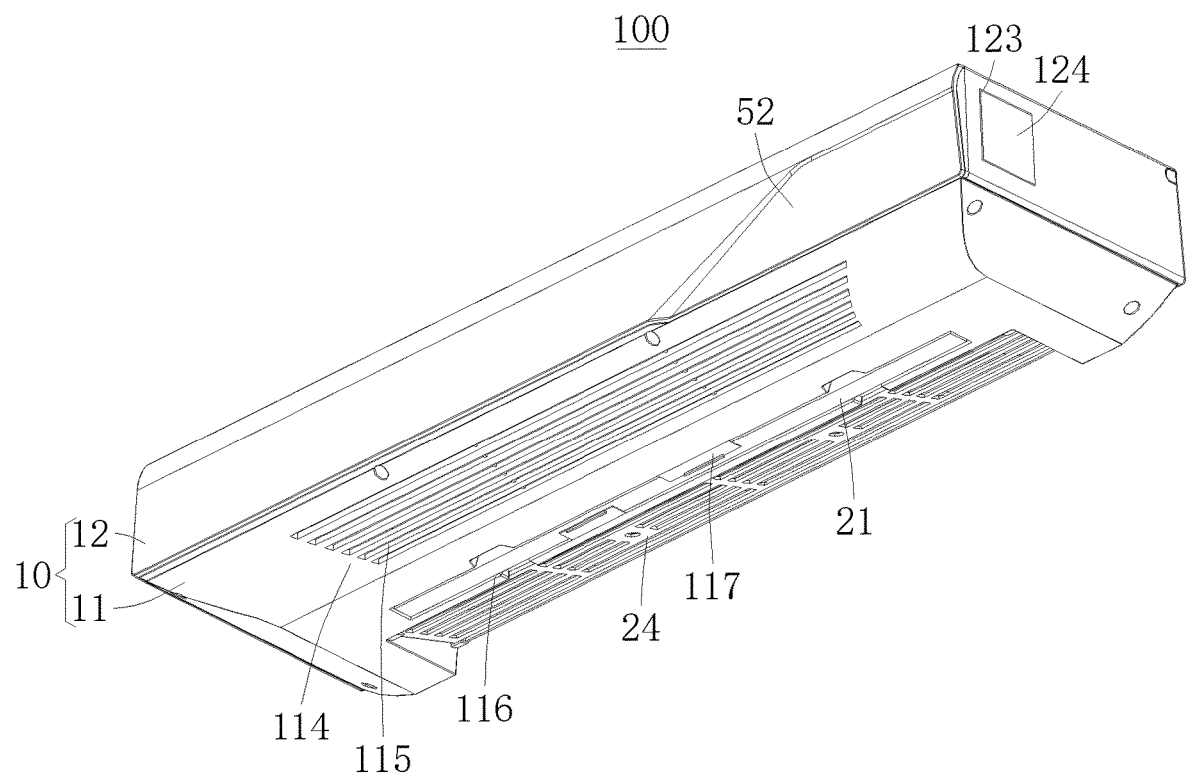
FIG. 17 is a schematic structural view of a wall-mounted air purifier provided in Embodiment 9 of this application.

In one embodiment, referring to FIG. 17, it is a three-dimensional structure view of the wall-mounted air purifier 100 of this embodiment. In this embodiment, the socket 116 is located at the bottom of the casing 10, a sliding plate 117 is provided in the socket 116, and the sliding plate 117 is slidably mounted on the bottom of the casing 10. When the filter 21 is inserted into the casing 10 through the socket 116, the sliding plate 117 can be pulled out so that the sliding plate 117 supports the filter 21; and when removing the filter 21, the sliding plate 117 is slid to be received in the casing 10, so that the filter 21 can be removed.

In one embodiment, referring to FIGS. 5 and 17, the ultraviolet lamp tube 411 is detachably mounted on the lamp holder 412, and the side of the casing 10 is provided with a window 123, and the casing 10 is mounted with a cover plate 124 covering the window 123. A window 123 is provided on the casing 10 so that the ultraviolet lamp tube 411 can be inserted and removed from the window 123 to facilitate the replacement of the ultraviolet lamp tube 411.

The wall-mounted air purifier 100 of the embodiment of the present application can not only filter and purify, but also sterilize and purify, and has a large air intake, and can provide purified air more quickly around the users.

The above are only alternative embodiments of this application and are not intended to limit this application. Any modification, equivalent replacement and improvement made within the spirit and principle of this application shall be included within the protection scope of this application.

What is claimed is:

1. A wall-mounted air purifier, comprising a casing, a filter mounted in the casing, and a fan mounted in the casing, the casing is provided with an air inlet and an air outlet, and the air outlet is located at a position corresponding to an outlet of the fan, the filter is located between the air inlet and the fan, wherein an ultraviolet light source and a light shield are further mounted in the casing, the light shield is covered on the ultraviolet light source, a side of the light shield close to the filter is open, and a first opening is formed on a side of the light shield away from the filter; and the ultraviolet light source is arranged between the air inlet and the fan; and
   wherein the light shield is provided with a blocking piece for blocking the first opening, and a second opening communicating with the first opening is formed between the blocking piece and the light shield.

2. The wall-mounted air purifier according to claim 1, wherein the ultraviolet light source is provided between the air inlet and the filter, and the light shield shields one side of the ultraviolet light source close to the air inlet.

3. The wall-mounted air purifier according to claim 1, wherein the light shield surrounds the ultraviolet light source, and a vent is provided on front and rear sides of the light shield.

4. The wall-mounted air purifier according to claim 1, wherein an inner surface of the light shield is provided with a reflective layer.

5. The wall-mounted air purifier according to claim 1, wherein the ultraviolet light source comprises an ultraviolet lamp tube and a lamp holder supporting the ultraviolet lamp tube, and the lamp holder is mounted in the casing.

6. The wall-mounted air purifier according to claim 5, wherein the ultraviolet lamp tube is detachably mounted on the lamp holder, and a side of the casing is provided with a window for disassembly and assembly of the ultraviolet lamp tube, a cover plate covering the window is mounted on the casing.

7. The wall-mounted air purifier according to claim 1, wherein the wall-mounted air purifier further comprises a filter mesh covering the air inlet, and the filter mesh is detachably mounted in the casing.

8. The wall-mounted air purifier according to claim 1, wherein the wall-mounted air purifier further comprises a negative ion generator which has an emitting head, and the emitting head is arranged at a corresponding position of the air outlet.

9. The wall-mounted air purifier according to claim 8, wherein the emitting head comprises a negative ion releasing brush arranged at the air outlet, a support for supporting the negative ion releasing brush, and two guide plates for guiding the diffusion of airflow, the support is mounted in the casing, the two guide plates are respectively arranged on opposite sides of the negative ion releasing brush, a distance between the two guide plates is gradually expanded from the middle of the guide plate to the lower side of the guide plate.

10. The wall-mounted air purifier according to claim 1, wherein the ultraviolet light source comprises an ultraviolet light emitting diode LED module which is mounted in the casing.

11. The wall-mounted air purifier according to claim 1, wherein the fan comprises a wind hood mounted in the casing, and a tubular wind wheel mounted in the wind hood and a motor driving rotation of the wind wheel.

12. The wall-mounted air purifier according to claim 1, wherein a front side of the casing is provided with a control panel which is inclined from top to bottom toward a rear side of the casing.

13. The wall-mounted air purifier according to claim 1, wherein the air inlet is located at a corresponding position on a rear side of a bottom of the casing, and the air outlet is provided at a corresponding position on a front side of the bottom of the casing.

14. The wall-mounted air purifier of claim 13, wherein the bottom of the casing has an inclined surface extending backward and upward, and the air inlet is provided on the inclined surface; and/or the bottom of the casing has an air outlet surface extending forward and upward, and the air outlet is provided on the air outlet surface.

15. The wall-mounted air purifier according to claim 14, wherein the bottom of the casing is provided with baffles protruding downwards at both ends of the inclined surface respectively.

16. The wall-mounted air purifier according to claim 1, wherein the casing is provided with a socket configured for allowing the filter to be plugged therein and unplugged therefrom, and the filter can be detachably inserted into the casing through the socket.

* * * * *